US007824462B2

(12) United States Patent
Webster et al.

(10) Patent No.: US 7,824,462 B2
(45) Date of Patent: Nov. 2, 2010

(54) METALLIC NANOPARTICLES AS ORTHOPEDIC BIOMATERIAL

(75) Inventors: Thomas J. Webster, Lafayette, IN (US); Jeremiah U. Ejiofor, Union, NJ (US)

(73) Assignee: Purdue Research Foundation, West Lafayette, IN (US)

( * ) Notice: Subject to any disclaimer, the term of this patent is extended or adjusted under 35 U.S.C. 154(b) by 1279 days.

(21) Appl. No.: 10/550,439

(22) PCT Filed: Mar. 26, 2004

(86) PCT No.: PCT/US2004/009358

§ 371 (c)(1),
(2), (4) Date: Sep. 22, 2005

(87) PCT Pub. No.: WO2004/085098

PCT Pub. Date: Oct. 7, 2004

(65) Prior Publication Data

US 2006/0204538 A1    Sep. 14, 2006

Related U.S. Application Data

(60) Provisional application No. 60/458,227, filed on Mar. 27, 2003.

(51) Int. Cl.
*B22F 3/02* (2006.01)
*A61F 2/02* (2006.01)
(52) U.S. Cl. .................... 75/245; 419/66; 623/11.11; 623/23.53; 977/931
(58) Field of Classification Search .............. 75/245; 623/11.11, 13.12, 23.53; 977/777, 931
See application file for complete search history.

(56) References Cited

U.S. PATENT DOCUMENTS

| | | | |
|---|---|---|---|
| 5,292,328 A | | 3/1994 | Hain et al. |
| 5,415,704 A | * | 5/1995 | Davidson .................. 148/316 |
| 5,733,337 A | | 3/1998 | Carr, Jr. et al. |
| 6,183,255 B1 | | 2/2001 | Oshida et al. |
| 6,319,264 B1 | | 11/2001 | Tormala et al. |
| 6,368,859 B1 | | 4/2002 | Atala |
| 6,572,672 B2 | * | 6/2003 | Yadav et al. ................. 75/343 |
| 6,669,706 B2 | | 12/2003 | Schmitt et al. |
| 2003/0040809 A1 | | 2/2003 | Goldmann et al. |
| 2004/0171323 A1 | | 9/2004 | Shalaby |
| 2004/0241211 A9 | | 12/2004 | Fischell et al. |

FOREIGN PATENT DOCUMENTS

WO    WO 01/55473    8/2001

OTHER PUBLICATIONS

International Search Report for International Application No. PCT/US2004/003958, International Filing Date Mar. 26, 2004. ISR completion date Nov. 24, 2004, Date of Mailing Jan. 5, 2005.
Wen et al., "Preparation of Bioactive Microporous Titanium Surface by a New Two-Step Chemical Treatment," Journal of Materials Science: Materials in Medicine, 9, 1998, pp. 121-128.
Larsson et al., "Bone response to surface modified titanium implants: studies on electropolished implants with different oxide thicknesses and morphology," Biomaterials, vol. 15, No. 13, 1994, pp. 1062-1074 and "Erratum," Biomaterials, vol. 16, No. 5, 1995, pp. 423.
Bordji et al, "Cytocompatibility of Ti-6Al-4V and Ti-5Al-2.5Fe Alloys According to Three Surface Treatments, Using Human Fibroblasts and Osteoblasts," Biomaterials, 17 (1990), pp. 929-940.
Sauberlich et al., "Cell culture tests for assaying the tolerance of soft tissue to variously modified titanium surfaces," Clin. Oral Impl. Res.10:379-393.
Siegel, Richard W., "Creating Nanophase Materials," Scientific American, Dec. 1996, pp. 74-79.
Klabunde et al., "Nanocrystals as Stoichiometric Reagents with Unique Surface Chemistry," J. Phys. Chem., 100 (1996), pp. 12142-12153.
Webster et al., "Specific proteins mediate enhanced osteoblast adhesion on nanophase ceramics," J. Biomed. Mat. Res., 51 (2000) pp. 475-783.
De Oliveira et al., "Nanotexturing of titanium-based surfaces upregulates expression of bone sialoprotein and osteopontin by cultured osteogenic cells," Biomaterials, 25 (2004), pp. 403-413.
Webster et al., "Mechanisms of Enhanced Osteoblast Adhesion on Nanophase Alumina Involve Vitronectin," Tissue Engineering, vol. 7, No. 3, 2001, pp. 291-307.
Buser et al., "Interface shear strength of titanium implants with a sandblasted and acid-etched surface; A biomechanical study in the maxilla of miniature pigs," J. Biomed. Mat. Res., 45 (1999) pp. 75-83.

(Continued)

*Primary Examiner*—Roy King
*Assistant Examiner*—Ngoclan T Mai
(74) *Attorney, Agent, or Firm*—Barnes & Thornburg LLP

(57) ABSTRACT

A composition for use as a prosthetic biomaterial and associated method. The biomaterial exhibits cytocompatibility, mechanical functionality and osteoblast adhesion between the implant and interfacing surface. The biomaterial is metallic, has a grain size less than about 500 nanometers and has a surface roughness of less than about 800 nm rms.

16 Claims, No Drawings

OTHER PUBLICATIONS

Orthopaedic Basic Science, Chapter 10, "Biomaterials," Sheldon Simon ed., Alan S. Litsky and Myron Spector, pp. 447-486.

Orthopaedic Basic Science, Chapter 4, "Form and Function of Bone," Sheldon Simon ed., Frederic S. Kaplan et al., pp. 127-184.

Kawaguchi et al., "Immunocytochemical and Lectin-Gold Characterization of the Interface Between Alveolar Bone and Implanted Hydroxyapatite in the Rat," Cells and Materials, vol. 3, No. 4, 1993, pp. 337-350.

Webster et al., "Osteoblast Adhesion on Nanophase Ceramics," Biomaterials, 20 (1990), 1221-1227.

Elias et al., "Enhanced Functions of Osteoblasts on Nanometer Diameter Carbon Fibers," Biomaterials, 23 (2002), 3279-3287.

Kay et al., "Nanostructured Polymer/Nanophase Ceramic Composites Enhance Osteoblast and Chondrocyte Adhesion," Tissue Engineering, vol. 8, No. 5, 2002, pp. 753-764.

Webster et al., "Design and Evaluation of Nanophase Alumina for Orthopaedic/Dental Applications," NanoStructured Materials, vol. 12, 1999, pp. 983-986.

Nishiguchi et al, "The effect of heat treatment on bone-bonding ability of alkali-treated titanium," Biomaterials, 20 (1999), pp. 491-500.

* cited by examiner

METALLIC NANOPARTICLES AS ORTHOPEDIC BIOMATERIAL

CROSS REFERENCE TO RELATED APPLICATION

This application is a U.S. national counterpart application of international application serial No. PCT/US2004/009358 filed Mar. 26, 2004, which claims priority to U.S. Provisional Patent Application No. 60/458,227 filed Mar. 27, 2003.

GOVERNMENT RIGHTS

Research relating to this invention was supported in part by the United States Government under Grant No. DMI0232597 awarded by the National Science Foundation. The U.S. Government may have certain rights in this invention.

FIELD OF THE INVENTION

This invention relates to a composition for use as a biomaterial for orthopedic implants and associated method and more particularly to a prosthetic biomaterial that includes metallic nanoparticles.

BACKGROUND OF THE INVENTION

Biomaterials, commonly used as implantable orthopedic prosthetic devices are not designed to retain functionality while maintaining compatibility with respect to biological factors at the implant/tissue interface. In order to achieve cytocompatability, it is desirable that the biomaterial surface characteristics at the interface be optimally compatible with pertinent bone cell types. Achieving similar mechanical properties to native tissue insures limited destruction of local cells. The surface texture of the biomaterial is also important to control for orthopedic implant efficacy to closely harmonize the mass and kinetics of the osseous biomolecular events. Previously implantable devices have been fabricated of ceramic, polymer, composite and metallic materials.

Metallic materials which have been used include titanium (Ti), a titanium alloy and a cobalt chromium molybdenum. These metallic materials have been found to have a grain size on the order of microns (μm).

Implant failures have been observed with each of these materials. Investigations have been run for the purpose of finding a technique for eliminating or at least reducing the incidents of bone implant failures in humans. The underperformance of implant has been blamed on incomplete osseointegration (i.e., lack of bonding of an orthopedic implant to a juxtaposed bone), stress shielding and/or the generation of wear debris at articulating surfaces.

Thus, it is desirable to increase the adhesion between the implant and tissue surface (sometimes referred to as osteoblast adhesion) particularly in connection with the metallic surfaces so as to address implant feature issues.

SUMMARY OF THE INVENTION

Biomaterials are commonly used in implantable orthopedic prosthetic applications are not designed to retain functionality while maintaining compatibility with respect to biological factors at the implant/tissue surface. In order to achieve cytocompatibility, it is desirable that the biomaterial surface characteristics at the interface be optimally compatible with the pertinent bone cell types. Achieving similar mechanical properties to native tissues insures limited destruction of local cells. The surface texture of the biomaterial is also important to control for orthopedic implant efficacy to closely harmonize with the mass and kinetics of osseous biomolecular events.

It has been found that osteoblast adhesion or adhesion at the metal/tissue interface can be increased by utilizing nanoparticle metals. These metals have a nanosize of less than 500 nm (nanometers) and usually between about 200 and 500 nm (nanometers). At this nano size, the metallic particles are similar in size to the cell size of the tissue under consideration. Moreover these metals have a surface roughness measured in rms nanometers of between about 11 and 360 nm rms. However, the roughness can be as great as 800 nm rms. In particular, titanium based metals such as commercially pure titanium, a titanium alloy (on a weight basis 11% Ti, 39% Al and 50% V) and a cobalt chrome molybdenum alloy (on a weight basis 3% Co 70% Cr and 27% Mo) can be successfully utilized. The composition of these metals on an atomic ratio basis can be expressed as Ti-6Al-4V and Co-28Cr-6Mo.

DETAILED DESCRIPTION

While the embodiments disclosed herein are susceptible to various modifications and alternative forms, specific embodiments will herein be described in detail. It will be understood, however, that there is no intent to limit the disclosure to the particular forms described, but on the contrary, the intention is to cover all modifications, equivalents and alternatives falling within the spirit and scope of the disclosure.

The current disclosure involves the use of nanoparticles of various metals such as titanium, titanium alloy (11% Ti, 89% Al and 80% V) and cobalt-chromium-molybdenum (3% Cr, 70% Cr and 27% Mo). Nanoparticles (less than 500 nm) having a surface roughness on the order of 11-356 rms nanometers have a high surface reactivity with tissue cells. As indicated above, the roughness can be up to 500 nm rms. In their properly consolidated form, nanoparticles result in increased elastic modules and strength as well as in nanostructured grains. These material formulations contain highly developed crystal grains fabricated out of their corresponding nanoparticles and possess properties (cytocompatibility and mechanical) that are appropriate for different orthopedic applications to the skeletal system. Most importantly, the nanophase metals significantly increase functions of cells that are responsible for bone adhesion (osteoblast adhesion) and bone tissue regeneration. Significantly increased adhesion and differentiation of bone cells as well as mineralization of the tissue are desirable to result in efficient and effective implants. For these reason, metallic nanoparticles are desirable as they closely match the mass and kinetics of bone/bodily fluid biomolecular reactions and enhance osseosus functions.

Nano size metal particles are available as a powder, formed by vapor deposition techniques and can be purchased from Power Tech Associates, 31 Flagship Drive, North Andover, Mass. 01845-6194. More specifically, these powders can include commercially pure titanium, the titanium alloy (such as Ti6Al4V) and the cobalt chrome molybdenum alloy 27% (Co-28Cr-6Mo). The material characteristics are shown in the Table below.

| Materials | Particle Size | Surface Roughness (RMS in Nanometers) | ASTM DESIGNATION |
|---|---|---|---|
| Ti | 500 Nanometers | 11.9 | F-67; G2 |
| Ti6Al4V | 500 Nanometers | 15.2 | F-136 |
| Co 28 Cr6 MO | 200 Nanometers | 356 | F-75; F-799 |

The powders indicated above can be commercially obtained.

These powders were obtained and loaded into a steel die and pressed at room temperature. One pressure, 10 giga pascals was used to press the titanium based compacts to a green density of 90-95%. The cobalt-chrome-molybdenum material was pressed at 5 giga pascals for 5 minutes to achieve the green density indicated above. The green disks which were produced by pressing were approximately 12 millimeters in diameter and between 0.50 and 1.1 millimeters thick. The surface characteristics of these metal compacts were characterized using scanning electromicroscopy (SEM) and atomic force microscopy (AFM) techniques. Using these techniques, the surface roughness was characterized using root mean square values expressed in nanometers as pointed out above.

Using these materials, osteoblast adhesion was determined. The general technique was to use human osteoblasts (bone forming cells; CLR 1137z American Culture Collection Population Nos. 6-12) which were seeded onto the substrates of interest and placed in standard cell culture conditions. That is a humidified, 5% Co2, 95% air environment for 1-3 hours. After the prescribed times, the substrates were rinsed, the remaining cells fixed and the remaining cells then examined and counted under a fluorescent microscope. Osteoblast morphology and adhesion locations of interest were examined using a scanning electron microscope (SEM).

The tests indicated an increased osteoblast adhesion to the nano sized particles and having a surface roughness indicated above. Particularly, it appeared that the osteoblasts formed on the grain boundaries of the materials. It is believed that the number of grain boundaries was increased due to the smaller size of the particles and the surface texture.

It has therefore been concluded that materials of a nanoparticle size and particularly having a texture as indicated above, increased the osteoblast formation and adhesion. The metals, more specifically the titanium titanium based alloys and cobalt based alloys) in powder form are believed to enhance implantation. It is appreciated that the powder material can be subjected to the various heat treatments and sintering processes of powder metallurgy. Moreover, the materials can be formed either as a unit or as a surface on a substrate in which surface interfaces with tissue.

While the disclosure has been illustrated and described in detail in the forgoing is considered to be as exemplary and not restrictive in character, it being understood that the illustrative embodiments have been described and it all changes in modifications that come within the spirit and scope of this disclosure are desired to be protected.

The invention claimed is:

1. A biomaterial for use in implantable orthopedic prosthetic devices wherein said biomaterial comprises consolidated nanoparticles and
   a. exhibits cytocompatibility with interfacing biological cells;
   b. exhibits mechanical functionality with interfacing biological cells;
   c. exhibits osteoblast adhesion between the implant and the interfacing biological cells; wherein the biomaterial
   d. is a metal;
   e. has a grain size less than about 500 nanometers; and
   f. has a surface roughness less than about 500 nanometers root mean square (nm rms).

2. A biomaterial as in claim 1 wherein the surface roughness is between 11 and 356 nanometers root mean square.

3. A biomaterial as in claim 2 which consists essentially of a titanium based metal.

4. A biomaterial as in claim 3 wherein the titanium based metal has a particle size of less than about 500 nanometers and a surface roughness of about 11 nanometers root mean square.

5. A biomaterial as in claim 4 wherein said titanium based metal is commercially pure titanium.

6. A biomaterial as in claim 1 wherein said metal is a titanium based alloy consisting essentially of, on a weight percent basis, of about 11% titanium, 39% aluminum and 50% vanadium.

7. A biomaterial as in claim 1 wherein the metal, on a weight percent basis, is a cobalt-chrome-molybdenum alloy consisting essentially of about 3% cobalt, 70% chromium and 27% molybdenum with the particle size less than about 200 nanometers and the surface roughness less than about 356 nanometers root mean square.

8. A biomaterial as in claim 1 wherein said metal is a powder.

9. A biomaterial as in claim 8 wherein said powder is consolidated and compressed so as to form a surface for interfacing with biological tissue.

10. A biomaterial as in claim 8 wherein said powder is compressed at room temperature.

11. A method of forming an implantable orthopedic prosthetic device including the steps of:
   (a) providing a metal biomaterial in powder form;
      1. which exhibits cytocompatibility within interfacing biological cells;
      2. exhibits mechanical functionality with interfacing biological cells; and
      3. exhibits osteoblast adhesion between the implant and interfacing biological cells;
   (b) compressing the powder in the absence of binders or sintering temperatures so as to form a consolidated composition comprising a surface for interfacing with biological cells, said consolidated composition having a grain size less than about 500 nanometers; and a surface roughness between about 11 and 360 nanometers root mean square.

12. A biomaterial for use in implantable orthopedic prosthetic devices wherein said biomaterial comprises consolidated nanoparticles and
   a. exhibits cytocompatibility with interfacing biological cells;
   b. exhibits mechanical functionality with interfacing biological cells;
   c. exhibits osteoblast adhesion between the implant and the interfacing biological cells; wherein the biomaterial
   d. is a metal; and
   e. has a particle size between 200 and 500 nanometers and a surface roughness between 11 and 360 nanometers root mean square.

13. A biomaterial for use in implantable orthopedic prosthetic devices wherein said biomaterial:
   a. exhibits cytocompatibility with interfacing biological cells;

b. exhibits mechanical functionality with interfacing biological cells;
c. exhibits osteoblast adhesion between the implant and the interfacing biological cells; wherein the biomaterial
d. is a metal;
e. has a particle size less than 500 nanometers, and
f. has a surface roughness less than 500 nanometers root mean square (nm rms).

14. A biomaterial as in claim 13 wherein the surface roughness is between 11 and 356 nanometers root mean square.

15. A biomaterial as in claim 14 which consists essentially of a titanium based metal.

16. A biomaterial as in claim 13 wherein the metal on a weight percent basis, is a cobalt-chrome-molybdenum alloy consisting essentially of about 3% cobalt, 70% chromium and 27% molybdenum with the surface roughness less than about 356 nanometers root mean square.

* * * * *